United States Patent
Hamman

(10) Patent No.: US 8,486,094 B2
(45) Date of Patent: Jul. 16, 2013

(54) SYSTEM AND METHOD FOR PROVIDING AN OBTURATOR FOR ENHANCED DIRECTIONAL CAPABILITIES IN A VASCULAR ENVIRONMENT

(75) Inventor: Baron L. Hamman, Dallas, TX (US)

(73) Assignee: Castlewood Surgical, Inc., Dallas, TX (US)

( * ) Notice: Subject to any disclaimer, the term of this patent is extended or adjusted under 35 U.S.C. 154(b) by 1418 days.

(21) Appl. No.: 11/842,541

(22) Filed: Aug. 21, 2007

(65) Prior Publication Data
US 2009/0054841 A1 Feb. 26, 2009

(51) Int. Cl.
*A61B 17/08* (2006.01)

(52) U.S. Cl.
USPC .......................................... 606/153; 606/213

(58) Field of Classification Search
USPC .. 606/151, 152, 153, 187, 213, 232; 607/126, 607/127
See application file for complete search history.

(56) References Cited

U.S. PATENT DOCUMENTS

| | | | |
|---|---|---|---|
| 4,222,380 A | | 9/1980 | Terayama |
| 4,770,176 A | * | 9/1988 | McGreevy et al. ............ 606/187 |
| 4,827,940 A | * | 5/1989 | Mayer et al. .................. 600/375 |
| 4,836,596 A | * | 6/1989 | Owen ........................... 294/99.2 |
| 5,042,161 A | | 8/1991 | Hodge |
| 5,053,041 A | | 10/1991 | Ansari et al. |
| 5,480,407 A | | 1/1996 | Wan et al. |
| 5,542,937 A | | 8/1996 | Chee et al. |
| 5,554,162 A | * | 9/1996 | DeLange ...................... 606/153 |
| 5,643,254 A | | 7/1997 | Scheldrup et al. |
| 5,669,905 A | | 9/1997 | Scheldrup et al. |
| 5,868,763 A | | 2/1999 | Spence et al. |
| 5,904,697 A | | 5/1999 | Gifford, III et al. |
| 5,944,728 A | | 8/1999 | Bates |
| 6,019,722 A | | 2/2000 | Spence et al. |
| 6,074,401 A | | 6/2000 | Gardiner et al. |
| 6,113,612 A | | 9/2000 | Swanson et al. |

(Continued)

FOREIGN PATENT DOCUMENTS

| | | |
|---|---|---|
| WO | WO 01/70119 A1 | 9/2001 |
| WO | WO 2011/068591 | 6/2011 |

OTHER PUBLICATIONS

Medtronic, "U-Clip™ Anastomotic Device and Spyder® Device," copyright Medtronic, Inc. 2007, http://www.medtronic.com/cardsurgery/products/uclip_spyder.html#, retrieved Oct. 30, 2009, 2 pages.

(Continued)

*Primary Examiner* — Tuan V Nguyen
(74) *Attorney, Agent, or Firm* — Patent Capital Group

(57) ABSTRACT

An apparatus for assisting in a vascular procedure includes an obturator operable to be mounted on a medical device to guide the medical device into a targeted region, whereby the obturator is substantially blunt such that it exhibits a snag-resistant property. In alternative embodiments, the apparatus includes an interface element operable to be used in conjunction with the obturator and to engage an interface of the targeted region such that pressure is maintained within the targeted region. The interface element includes a convex portion that operates to seat the interface element at a selected location. The interface element is substantially transparent and includes a magnification element that magnifies materials underlying the interface element. In other embodiments, the apparatus includes a tray operable to provide a mold for forming the obturator, which may include a gas, water, sugar, clotted blood, a gelatinous material, a protein, a saline solution, or dry-ice.

8 Claims, 5 Drawing Sheets

U.S. PATENT DOCUMENTS

| | | | |
|---|---|---|---|
| 6,149,658 | A | 11/2000 | Gardiner et al. |
| 6,165,186 | A | 12/2000 | Fogarty et al. |
| 6,193,734 | B1 | 2/2001 | Bolduc et al. |
| 6,206,827 | B1 | 3/2001 | Chin et al. |
| 6,224,619 | B1 | 5/2001 | Hill |
| 6,251,092 | B1 | 6/2001 | Qin et al. |
| 6,309,416 | B1 | 10/2001 | Swanson et al. |
| 6,352,543 | B1 | 3/2002 | Cole |
| 6,368,341 | B1 | 4/2002 | Abrahamson |
| 6,440,163 | B1 | 8/2002 | Swanson et al. |
| 6,508,822 | B1 | 1/2003 | Peterson et al. |
| 6,514,265 | B2 | 2/2003 | Ho et al. |
| 6,517,558 | B2 | 2/2003 | Gittings et al. |
| 6,533,812 | B2 | 3/2003 | Swanson et al. |
| 6,551,314 | B1 | 4/2003 | Hill et al. |
| 6,551,332 | B1 | 4/2003 | Nguyen et al. |
| 6,565,582 | B2 | 5/2003 | Gifford, III et al. |
| 6,575,985 | B2 | 6/2003 | Knight et al. |
| 6,605,104 | B2 | 8/2003 | Sato et al. |
| 6,607,541 | B1 | 8/2003 | Gardiner et al. |
| 6,613,059 | B2 | 9/2003 | Schaller et al. |
| 6,620,177 | B2 | 9/2003 | Buelna et al. |
| 6,635,214 | B2 | 10/2003 | Rapacki et al. |
| 6,641,593 | B1 | 11/2003 | Schaller et al. |
| 6,652,540 | B1 | 11/2003 | Cole et al. |
| 6,660,015 | B1 | 12/2003 | Berg et al. |
| 6,673,085 | B1 | 1/2004 | Berg |
| 6,695,859 | B1 | 2/2004 | Golden et al. |
| 6,699,256 | B1 | 3/2004 | Logan et al. |
| 6,699,257 | B2 | 3/2004 | Gifford, III et al. |
| 6,702,829 | B2 | 3/2004 | Bachinski et al. |
| 6,719,768 | B1 | 4/2004 | Cole et al. |
| 6,723,038 | B1 | 4/2004 | Schroeder et al. |
| 6,730,103 | B2 | 5/2004 | Dakov |
| 6,743,169 | B1 | 6/2004 | Taylor et al. |
| 6,743,170 | B1 | 6/2004 | Spence et al. |
| 6,802,847 | B1 | 10/2004 | Carson et al. |
| 6,802,848 | B2 | 10/2004 | Anderson et al. |
| 6,808,498 | B2 | 10/2004 | Laroya et al. |
| 6,814,743 | B2 | 11/2004 | Chin et al. |
| 6,960,217 | B2 | 11/2005 | Bolduc |
| 7,063,711 | B1 | 6/2006 | Loshakove et al. |
| 7,122,040 | B2 | 10/2006 | Hill et al. |
| 7,150,742 | B2 | 12/2006 | Takamoto et al. |
| 7,212,870 | B1 * | 5/2007 | Helland ............ 607/127 |
| 7,294,139 | B1 | 11/2007 | Gengler |
| 7,763,037 | B2 | 7/2010 | Hamman |
| 2002/0077636 | A1 | 6/2002 | Arcia et al. |
| 2003/0120291 | A1 | 6/2003 | Chin et al. |
| 2003/0125755 | A1 | 7/2003 | Schaller et al. |
| 2003/0176878 | A1 | 9/2003 | Bolduc et al. |
| 2003/0208214 | A1 | 11/2003 | Loshakove et al. |
| 2004/0068276 | A1 | 4/2004 | Golden et al. |
| 2004/0127919 | A1 | 7/2004 | Trout et al. |
| 2005/0043749 | A1 | 2/2005 | Breton et al. |
| 2005/0070924 | A1 | 3/2005 | Schaller et al. |
| 2005/0277958 | A1 | 12/2005 | Levinson |
| 2006/0025788 | A1 | 2/2006 | Loshakove et al. |
| 2006/0212066 | A1 | 9/2006 | Hamman |
| 2009/0018555 | A1 | 1/2009 | Hamman |
| 2009/0076454 | A1 | 3/2009 | Hamman et al. |
| 2009/0093825 | A1 | 4/2009 | Logan |
| 2011/0130624 | A1 | 6/2011 | Hamman et al. |

OTHER PUBLICATIONS

Novare Surgical, "Enclose® II Anastomosis Assist Device," copyright 2009 Novare Surgical Systems, Inc., http://www.novaresurgical.com/enclose2/enclose2device/, retrieved Oct. 30, 2009, 1 page.

MedGadget, "Heartstring III Proximal Seal System for CABG," Apr. 14, 2008, copyright 2004-2009 Medgadget LLC, http://medgadget.com/archives/2008/04/heartstring_iii-proximal_seal_system_for_cabg.html, retrieved Oct. 30, 2009, 6 pages.

USPTO Nonfinal Office Action dated Aug. 15, 2007 for U.S. Appl. No. 11/084,453 filed Mar. 18, 2005, 8 pages.

USPTO Final Office Action dated Jan. 10, 2008 for U.S. Appl. No. 11/084,453, filed Mar. 18, 2005, 7 pages.

USPTO Nonfinal Office Action dated Apr. 22, 2008 for U.S. Appl. No. 11/084,453, filed Mar. 18, 2005, 9 pages.

U.S. Appl. No. 12/629,656, filed Dec. 2, 2009 entitled "System and Method for Attaching a Vessel in a Vascular Environment," Inventor(s) Baron L. Hamman, et al.

Tappainer, Ernesto, "New Device for Saphenous Vein-to-Aorta Proximal Anastomosis Without Side-Clamping," Journal of Cardiothoracic Surgery, Apr. 17, 2007, 31 pgs.

R.K. Wolf, M.D., "Anastomotic Devices for Coronary Surgery," May 2004, 7 pgs.

Non-Final Office Action in U.S. Appl. No. 12/273,484 mailed on Apr. 15, 2011.

Response to Non-Final Office Action dated Apr. 15, 2011 in U.S. Appl. No. 12/273,484 filed on Jul. 15, 2011.

Final Office Action in U.S. Appl. No. 12/332,058 mailed on Jun. 16, 2011.

Non-Final Office Action in U.S. Appl. No. 12/273,494 mailed on Apr. 15, 2011.

Response to Non-Final Office Action dated Apr. 15, 2011 in U.S. Appl. No. 12/273,494 filed on Jul. 14, 2011.

Non-Final Office Action from U.S. Appl. No. 12/332,058 mailed on Jan. 14, 2011.

Response to Non-Final Office Action dated Jan. 14, 2011 in U.S. Appl. No. 12/332,058 filed on Apr. 14, 2011.

Final Office Action in U.S. Appl. No. 12/332,508 mailed on Jun. 14, 2011.

USPTO Oct. 17, 2010 Response to Aug. 15, 2007 Non-Final Office Action from U.S. Appl. No. 11/084,453.

USPTO Feb. 21, 2008 RCE Response to Jan. 10, 2008 Final Office Action from U.S. Appl. No. 11/084,453.

USPTO Jun. 10, 2008 Response to Apr. 22, 2008 Non-Final Office Action from U.S. Appl. No. 11/084,453.

USPTO Sep. 2, 2008 Final Office Action from U.S. Appl. No. 11/084,453.

USPTO Sep. 22, 2008 RCE Response to Sep. 2, 2008 Final Office Action from U.S. Appl. No. 11/084,453.

USPTO Dec. 9, 2008 Non-Final Office Action from U.S. Appl. No. 11/084,453.

USPTO Dec. 22, 2008 Response to Dec. 9, 2008 Non-Final Office Action from U.S. Appl. No. 11/084,453.

USPTO Mar. 16, 2009 Final Office Action from U.S. Appl. No. 11/084,453.

USPTO Mar. 27, 2009 RCE Response to Mar. 16, 2009 Final Office Action from U.S. Appl. No. 11/084,453.

USPTO Jun. 17, 2009 Non-Final Office Action from U.S. Appl. No. 11/084,453.

USPTO Sep. 17, 2009 Response to Jun. 17, 2009 Non-Final Office Action from U.S. Appl. No. 11/084,453.

USPTO Jan. 7, 2010 Final Office Action from U.S. Appl. No. 11/084,453.

USPTO Mar. 9, 2010 Appeal Brief Office Action from U.S. Appl. No. 11/084,453.

USPTO Jun. 2, 2010 Notice of Allowance from U.S. Appl. No. 11/084,453.

USPTO Apr. 15, 2011 Non-Final Office Action from U.S. Appl. No. Nov. 18, 2008.

Notification of Transmittal of the International Search Report and the Written Opinion of the International Searching Authority, or the Declaration (1 page), International Search Report (6 pages), and Written Opinion (8 pages) for International Application No. PCT/US2010/052253 mailed Jan. 26, 2011.

* cited by examiner

SYSTEM AND METHOD FOR PROVIDING AN OBTURATOR FOR ENHANCED DIRECTIONAL CAPABILITIES IN A VASCULAR ENVIRONMENT

TECHNICAL FIELD OF THE INVENTION

This invention relates in general to the field of cardiac and vascular surgery and, more particularly, to a process, a system, and a method for providing an obturator for enhanced directional capabilities in a vascular environment.

BACKGROUND OF THE INVENTION

In recent decades, the treatment of vascular diseases has grown exponentially in terms of sophistication and diversity. Most cardio-thoracic procedures, bypasses, and valve surgeries are routine, almost commonplace. Their popularity is due, in part, to their tremendous success rates and their ability to offer extraordinary benefits to a patient. Other types of surgeries have achieved a similar level of acceptance and popularity.

Many such procedures involve the use of medical devices, which have experienced considerable notoriety in recent years. Although these devices can automate and improve various types of procedures, many of these instruments do suffer from a number of significant drawbacks. For example, many medical devices include sharp points at their points of contact: points that generally snag or tear surrounding areas of tissue. In cases where an injury occurs, the surrounding tissue may be prone to inflammation, trauma, infection, or incomplete seals that can lead to bleeding and stroke. This detracts from the value of the surgery, adds unnecessary risk for a patient, and forces a surgeon to exercise extraordinary diligence in using such devices. Therefore, optimizing or simplifying any of these problematic issues may yield a significant reduction in risk for a patient and, further, minimize the accompanying burden for a surgeon.

Because a surgeon is generally tasked with estimating the approximate location of a target operating region [and in some cases, feeling his way through potential blind-spots], enhancing the accuracy of the placement of a given medical device would be highly beneficial and welcomed.

Accordingly, the ability to provide an effective medical tool that properly accounts for the aforementioned problems presents a significant challenge for component manufactures, system designers, and physicians alike.

SUMMARY OF THE INVENTION

From the foregoing, it may be appreciated by those skilled in the art that a need has arisen for an improved instrument or tool for achieving superior control, management, and performance during a given procedure. In accordance with an embodiment of the present invention, a device, a system, and a method for enhancing an operation are provided that includes a flexible, precise, easy-to-use element, which substantially eliminates or greatly reduces disadvantages and problems associated with conventional equipment and instruments.

According to an embodiment of the present invention, an apparatus for assisting in a vascular procedure is provided that includes an obturator operable to be mounted on [or within] a medical device to guide the medical device into a targeted region, whereby the obturator is substantially blunt such that it exhibits a snag-resistant property.

In alternative embodiments, the apparatus includes an interface element operable to be used in conjunction with the obturator [or another device], whereby it can be used to engage an interface of the targeted region such that pressure is maintained within the targeted region. The interface element includes a convex portion that operates to seat the interface element at a selected location, which may be a round, oblong, or cut hole. The interface element is substantially transparent and includes a magnification element that magnifies materials underlying the interface element so as to see the underlying hole or incision. In other embodiments, the apparatus includes a tray operable to provide a mold for forming the obturator, which may comprise a gas, water, sugar, clotted blood, a gelatinous material, a protein, a saline solution, and dry-ice.

In specific embodiments, the obturator is operable to be used in conjunction with a medical device that includes one or more sharp or pointed legs. The legs of the medical device each include a tip that is sharp and operable to pierce the obturator such that it can be secured and transported.

Certain embodiments of the present invention may provide a number of technical advantages. For example, according to one embodiment of the present invention, an architecture and a process are provided that offer a flexible system, which can easily accommodate any number of diverse surgeries. The obturator serves as a blunt instrument for directing an accompanying medical device. The obturator is blunt enough to avoid snagging a given tool or instrument in undesired locations; however, the obturator is pointed enough to give some guidance or directional capabilities for an accompanying device. This offers a high degree of accuracy in placing a given tool or instrument. In essence, the obturator eliminates the need for retrieving the initial item that allowed for a viable entrance (or pathway) into the surgical area.

In addition, the obturator is dissolvable: operating almost as a hologram in disappearing after a given time period so that if it breaks off and ventures into the bloodstream, it is of no consequence (i.e. no strokes or damage done to an end-organ). The time period is configurable, as the solubility of the obturator can be based on the chemicals used in the obturator, or it can be temperature-based. The obturator is further advantageous because it does not contaminate the interior of a given vessel or vein: such contact normally harms these sensitive items. Additional advantages are described herein with reference to corresponding FIGURES.

In another embodiment of the invention, the lens/device [being transparent] functions as a barrier to the contents of the hollow organ (e.g., aorta and blood), which allows the surgeon to carefully aim his device in a way that, on swift removal, allows the surgeon to insert/place that device into a hole that would otherwise be obscured by egressing blood (or gas, organ contents, etc.).

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which.

DETAILED DESCRIPTION OF THE INVENTION

Figure 1:
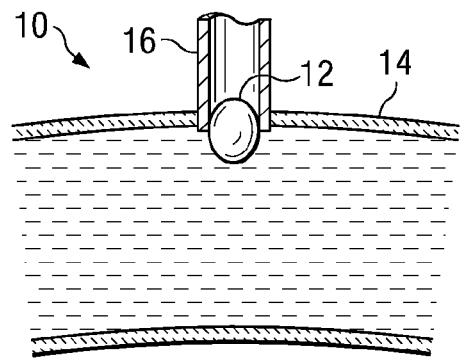
FIG. 1 is a simplified schematic diagram illustrating an obturator to be used in a procedure in accordance with one embodiment of the present invention.

FIG. 1 is a simplified schematic diagram of an example vascular environment 10 in which an obturator 12 may be used during a given operation. In this first example, obturator 12 is being used in connection with an anastomosis between a tube 16 (or a vein, or a vessel, etc.) and a second conduit 14 (e.g., an aorta).

Note that the outer layer of the aorta is generally susceptible to trauma and inflammation. Specifically, devices such as cutters or vein-holding instruments (as illustrated in FIG. 4F) can easily become entangled while attempting to engage a hole or while making an incision. A high level of precision is necessary to avoid snagging in any area that surrounds the target area. In cases where entanglement does occur, a patient could suffer blood loss or, in other scenarios, a surgeon could inadvertently make an errant hole or a tear in surrounding tissue of the surgical area.

A few strategies may be employed to address this worrisome issue. One remedy, which is specific to a vein-holding apparatus inclusive of multiple needles, would allow all the needles to converge to a single point. This would allow a surgeon to effectively place a single needle, as opposed to a group of prickly ends, into a single destination. In this manner, the device becomes stream-lined: albeit in only one direction.

The present invention takes a different approach in offering an ideal obturator 12 that serves as a blunt instrument for directing an accompanying medical device. Obturator 12 is blunt enough to avoid snagging a given tool or instrument; however, obturator 12 is pointed enough to give some guidance or directional capabilities for an accompanying device. In this given example of FIG. 1, obturator 12 is being used in conjunction with a vein-holding apparatus such as that which is provided by Pending patent application having Ser. No. 11/084,453 and Entitled: System and Method For Attaching a Vein, an Artery, or a Tube in a Vascular Environment [filed Mar. 18, 2005], which is hereby incorporated by reference herein in its entirety. In this example, the obturator is sized based on the vein's diameter: approximately 2-9 millimeters. However, this range has only been offered for example purposes and can certainly be changed to accommodate other arrangements based on particular needs.

Obturator 12 can be dissolvable: operating almost as a hologram in disappearing after a given time period. The time period is configurable, as the solubility of obturator 12 can be based on the chemicals used in obturator 12 or it can be based on how frozen obturator 12 is made to be (or its intrinsic temperature). Obviously, this frozen rigidity will dissolve when exposed to other external elements, such as a person's blood, or the ambient temperature of the operation room.

Obturator 12 is further advantageous because it does not contaminate the interior of a given vessel or vein: such contact normally harms these sensitive items. Obturator 12 can be employed such that harmful touching is effectively avoided. Obturator 12 may be constructed of a gas, water, sugar, clotted blood, a gelatinous material, a protein, a saline solution, dry-ice, or any suitable combination thereof. Obturator 12 would dissolve in a time that would be short enough to minimize the potential for having a stroke. For example, the total time to dissolve may be about 2:00 minutes. However, obturator 12 could be used to offer any suitable time period for dissolution.

In essence, obturator 12 can allow a surgeon to gain entrance into a given organ, while effectively eliminating the original, entrance obturator. The initial obturator effectively disappears: without any additional effort from the surgeon. This could be important for gaining access to the apex of the heart, or in the field of robotics, or in remote vascular procedures, or in instances where something is propped up or glued or fixed by the surgeon. The common theme here is an elimination of the need for retrieving the initial item that allowed for an entrance into the surgical area. The advantage of obturator 12 is that it achieves a stream-lined effect in a first direction, but does not suffer from a difficult removal in the second direction (i.e. during exit).

Figure 2A:
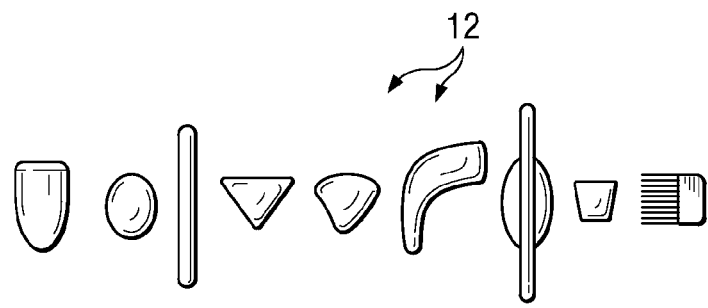
FIG. 2A is a simplified block diagram of an example set of potential shapes that a given obturator could take.

FIG. 2A is a simplified block diagram of an example set of potential shapes that a given obturator could take. Some of these include comb shapes (which would prohibit a predetermined amount of blood flow from exiting a given area, while potentially allowing legs of given device to penetrate some of the seams of the comb), bullet shapes, triangular shapes, etc. Note that these shapes are not exhaustive and are only being provided in hopes of offering some example configurations to be used in accordance with the present invention.

Figure 2B:
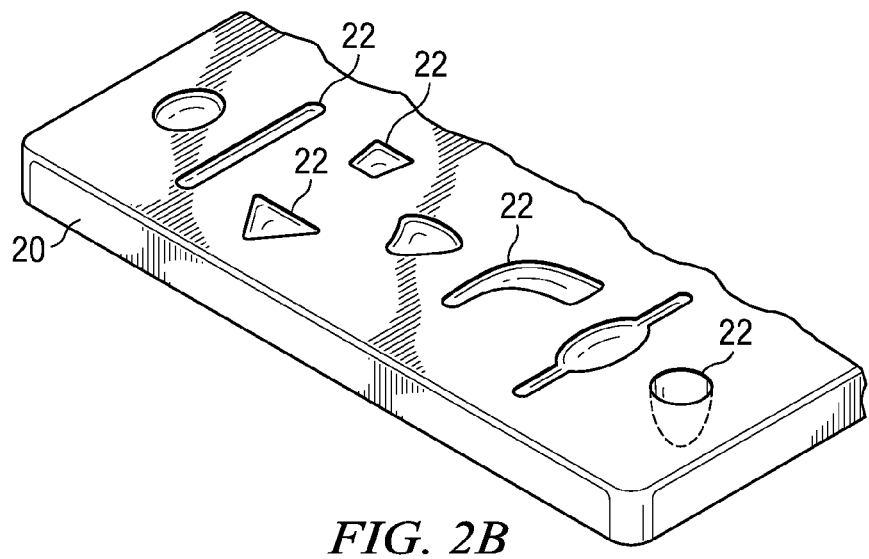
FIG. 2B is a simplified block diagram of an example tray for forming the shapes for the obturators of FIG. 2A.

FIG. 2B is a simplified block diagram of a tray 20 for forming the shapes for the obturator of FIG. 2A. A set of molds 22 are provided to illustrate how the obturator may be formed. Tray 20 may simply be placed in a refrigerating compartment (or other suitable cooling mechanism) such that the obturator becomes solid. Note that most hospital rooms that are used to accommodate surgical procedures include a small water freezer or slush machine that could certainly be used to fulfill this purpose.

Figure 3A:
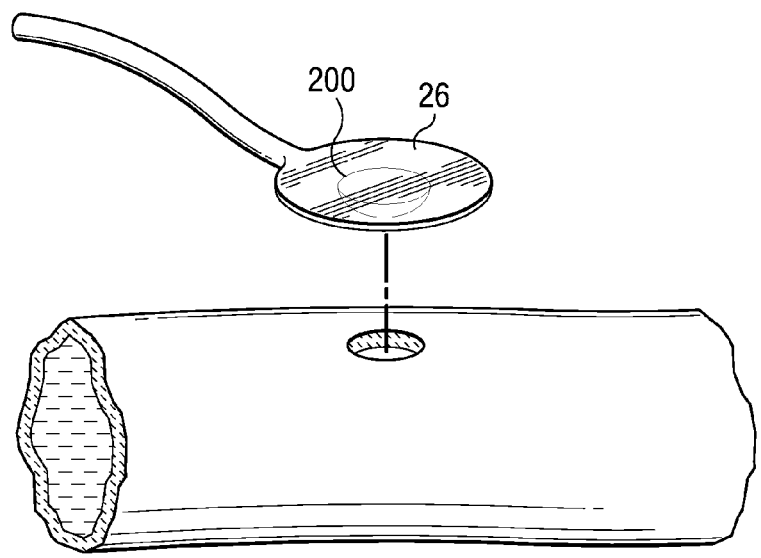
FIGS. 3A-3C are simplified block diagrams illustrating an interface tool that is operable to assist a surgeon in placing a given device: either with or without the obturator.
Figure 3B:
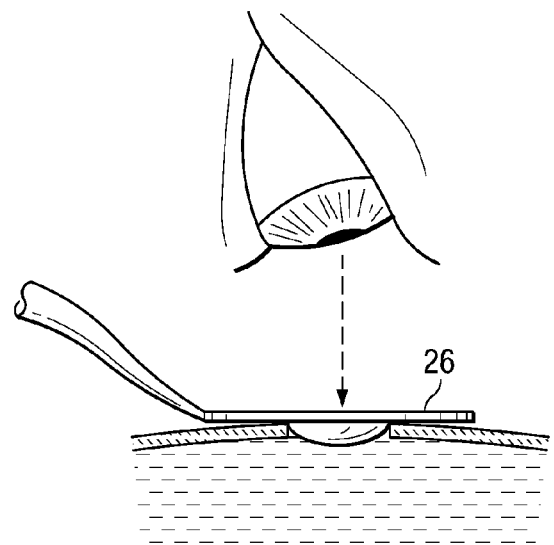
Figure 3C:
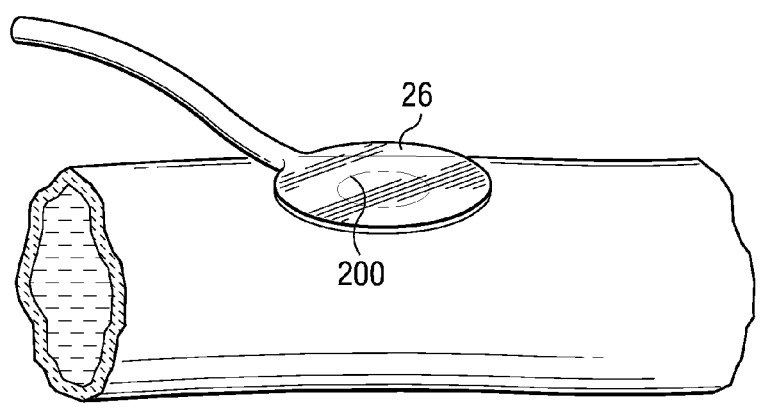

FIGS. 3A-3C are simplified block diagrams illustrating an interface tool 26 that is operable to assist a surgeon in placing a given device: either with or without obturator 12. As illustrated, interface tool 26 may be transparent (or oblique or opaque in other embodiments) and may include a magnification element such that a surgeon may see the underlying element in greater detail. Interface tool 26 may include a convex portion 200 (this may or may not include the magnification element). In cases where there is a hole provided in the underlying issue, convex portion 200 may operate to seat interface tool 26 into the surface. In this sense, a surgeon can feel his way into an opening, as convex portion 200 engages the surface area of the targeted location and is suitably secured thereon. In action, interface tool 26 may be used to suppress blood flow (or other fluids) from escaping from the underlying tissue. In this sense, interface tool 26 maintains the interior pressure and may be used as a stop-gap until the attending surgeon is prepared to address the targeted area or the incised hole.

Before proceeding further, for purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

The basic tenets of vascular operations allow us to appreciate that surgeries can be highly invasive and, therefore, present a number of risks. For example, existing devices that are used in many current operations can be difficult to control, as the surgeon must have extraordinary dexterity in manipulating the requisite components. In other scenarios, devices may offer benefits associated with ease of use; but these devices are generally flawed because they often improperly violate the inside of the aorta or facilitate entanglement problems. In the context of bypass procedures, contact with the aorta should be avoided because plaque or any other (potentially friable) detrimental element can flake off and become dislodged in other anatomical locations.

Obturator 12 overcomes the aforementioned deficiencies, as well as others, in providing an optimal solution for a physician who is relegated the difficult task of performing a vascular procedure. Obturator 12 is intuitive in that it guides an accompanying device and, further, offers exceptional flexibility and adaptability for a physician. In addition, obturator 12 offers enhanced accuracy for a surgeon who must make precise incisions (e.g., in the aortic wall, or the apex of the heart, etc.). No longer would a surgeon have to guess or to estimate the location of a given hole in an organ or in a piece of tissue. Additionally, such an instrument is minimally invasive because removal of obturator 12 (because of its solubility) is no longer necessary.

Figure 4A:
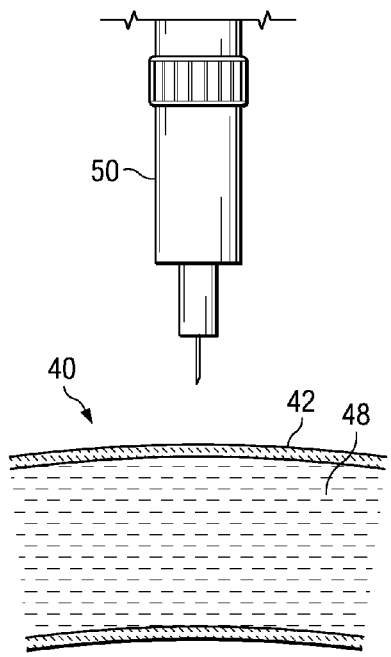
FIGS. 4A-J are simplified schematic diagrams of another example operation that implicates the obturator.
Figure 4B:
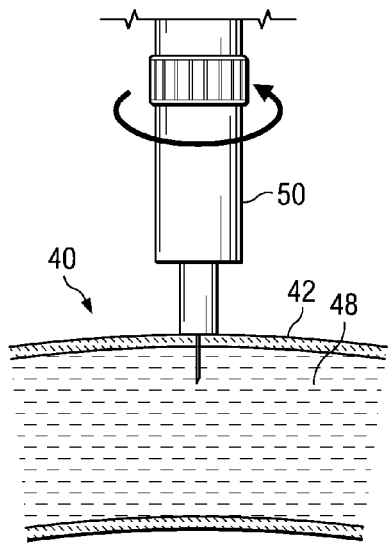
Figure 4C:
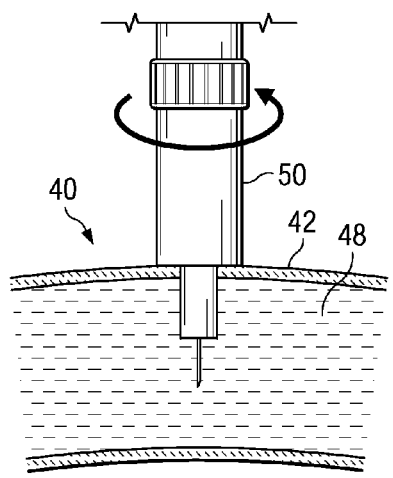
Figure 4D:
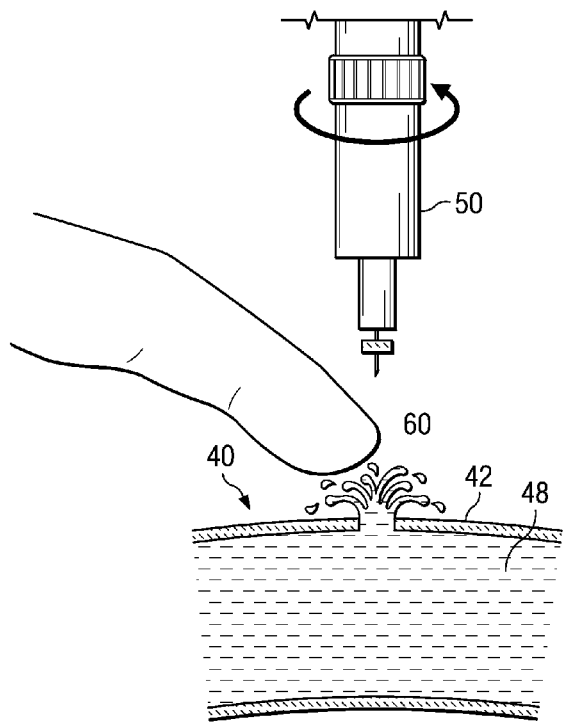
Figure 4E:
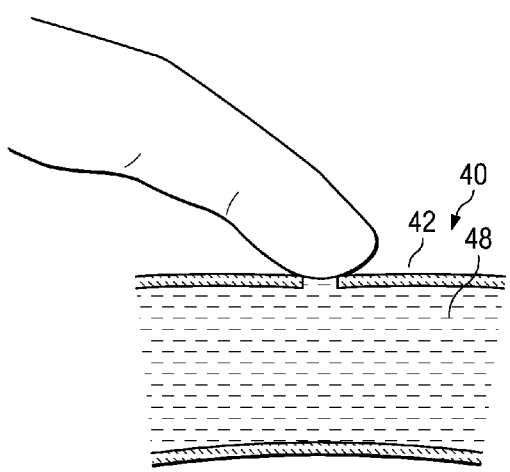
Figure 4F:
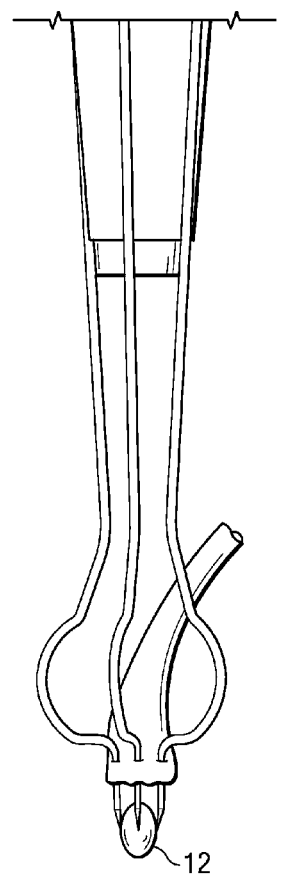

FIGS. 4A-J illustrate how a hole may be cut in an aortic wall 40. FIG. 4A includes a cutter 50, which may be used to make a small incision into the aorta. FIG. 4A also illustrates blood flow 48, as well as an initial aortic layer 42, which is penetrated by cutter 50. The aortic cutter 50 is used to make a uniform hole in the aorta for attaching the vein bypass graft.

FIG. 4B illustrates cutter 50 being engaged, whereby layer 42 is pierced. FIG. 4C illustrates cutter 50 being suitably positioned within aortic wall 40 just before the hole is actually cut. FIG. 4D illustrates the hole that was created and the resulting blood flow. Cutter 50 may be automatic or mechanical, as its rotation can produce a uniform incision in either case. Because of the blood flow, the surgeon can simply put his finger over the hole prior to plugging the hole with the vein, as is illustrated by FIG. 4E. FIG. 4F illustrates how obturator 12 can be grasped by a medical instrument such that obturator 12 can be used to guide the device to a targeted area: free from snagging in undesirable locations.

Figure 4G:
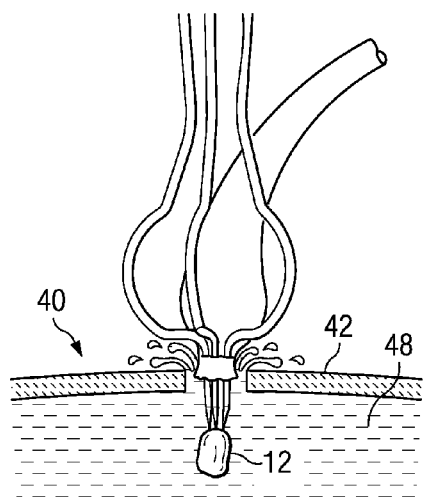
Figure 4H:
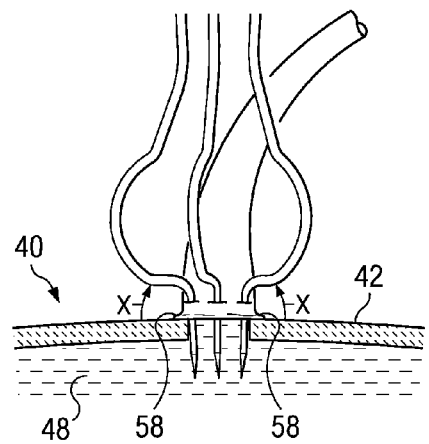

FIGS. 4G through 4J illustrate a transfer operation in which the vein is used to fill the void in the aortic wall. This process involves the proximal attachment, whereas the distal attachment involves a separate procedure. FIG. 4G illustrates how the hole is plugged with a medical device, which now includes a loaded vein. Note that obturator 12 is within the tissue, as it begins to dissolve and erode from its original form. At this stage, the legs of the medical device are somewhat close together and the vein is compressed. A handle can then be pulled or pushed such that the legs are somewhat extended and the vein is, thereby, expanded, as is shown in FIG. 4H. Obturator 12 is completely dissolved at this point such that the surgeon does not need to worry about retrieving the original obturator 12, which facilitated entry into the target location.

Note that there is some pressure in the vein such that, once suitably positioned, the vein will inflate to capacity. FIG. 4H further illustrates the design consideration that is given to the legs. An angle 'X' is created between aortic wall 42 and the legs. This enables a lip 58 of the vein to be produced, which can further enable the suturing process.

Figure 4I:
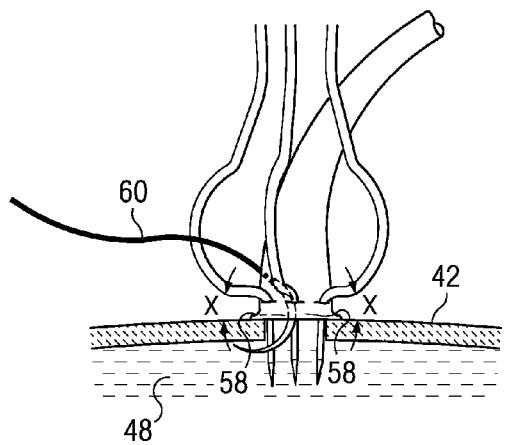

FIG. 4I illustrates the seal that is formed, whereby the vein is taut and ready to be sutured to the aorta. FIG. 4I illustrates a first suture 60 being positioned around the vein. Alternatively, a clip or some other mechanism may be used to join these two interfaces. Sutures may be ideal because they are benign and because they offer a simple protocol for the surgeon.

Figure 4J:
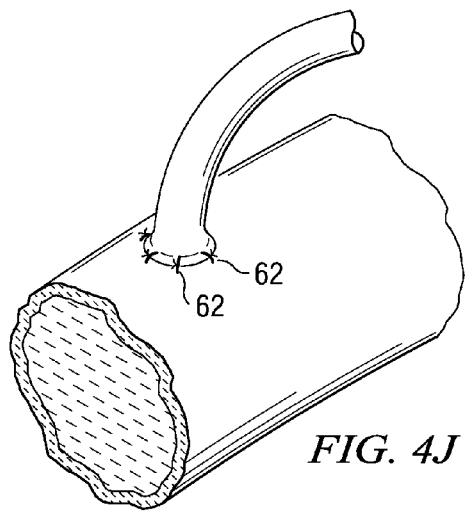

FIG. 4J illustrates a series of sutures 62 having been properly placed around the bypass vein. The suturing operation was assisted by the design of the legs, whereby such a fastening procedure provides a reliable means for securing the vein to the aortic wall. Utilizing such a suturing approach achieves some level of comfort for the tending surgeon, as suturing represents a customary method of accomplishing such an attachment. Thus, obturator 12 has provided a virtually seamless entry and exit for the surgeon at the targeted surgical site.

Note that any of the previously discussed materials could be included in a given kit, which could ostensibly be provided to a physician who is responsible for performing a procedure. A basic kit could include a given medical device, obturator 12, and interface element 26. The kit could also include one or more closures for suturing or affixing the vein or tube. Any of these components may be manufactured based on particular specifications or specific patient needs. The present invention contemplates considerable flexibility in such components, as any permutation or modification to any of these elements is clearly within the broad scope of the present invention.

It is important to note that the stages and steps in the preceding FIGURES illustrate only some of the possible scenarios that may be executed by, or within, the architecture of the present invention. Some of these stages and/or steps may be deleted or removed where appropriate, or these stages and/or steps may be modified or changed considerably without departing from the scope of the present invention. In addition, a number of these operations have been described as being executed concurrently with, or in parallel to, one or more additional operations. However, the timing of these operations may be altered considerably. The preceding example flows have been offered for purposes of teaching and discussion. Substantial flexibility is provided by the proffered architecture in that any suitable arrangements, chronologies, configurations, and timing mechanisms may be provided without departing from the broad scope of the present invention.

Note also that the example embodiments described above can be replaced with a number of potential alternatives where appropriate. The processes and configurations discussed herein only offer some of the numerous potential applications of the device of the present invention. The elements and operations listed in FIGS. 1-4J may be achieved with use of the present invention in any number of contexts and applications. Accordingly, suitable infrastructure may be included within a given system (or cooperate with obturator 12 in some fashion) to effectuate the tasks and operations of the elements and activities associated with managing a procedure.

Although the present invention has been described in detail with reference to particular embodiments in FIGS. 1-4J, it should be understood that various other changes, substitutions, and alterations may be made hereto without departing from the sphere and scope of the present invention. For example, although the preceding FIGURES have referenced a number of components as participating in the numerous outlined procedures, any suitable equipment or relevant tools may be readily substituted for such elements and, similarly, benefit from the teachings of the present invention. These may be identified on a case-by-case basis, whereby a certain patient may present a health risk factor while another (with the same condition) may not. Hence, the present tool may be designed based on particular needs with particular scenarios envisioned.

It is also imperative to note that although the present invention is illustrated as implicating several example procedures, this has only been done for purposes of example. The present invention could readily be used in virtually any procedure where an obturator would be beneficial and, accordingly, should be construed as such. The present invention may easily be used to provide a viable vascular management solution at various locations of the mammalian anatomy, which are not necessarily illustrated by the preceding FIGURES.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims. In order to assist the United States Patent and Trademark Office (USPTO) and additionally any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of filing hereof unless the words "means for" are specifically used in the particular claims; and (b) does not intend by any statement in the specification to limit his invention in any way that is not otherwise reflected in the appended claims.

What is claimed is:

1. A system to be used in a vascular environment, comprising:
   a medical device having a plurality of tips; and
   an obturator having a rounded shape and an outer surface grasped by the plurality of tips of the medical device such that the obturator is secured,
   wherein the obturator is operable to guide the plurality of tips of the medical device into a targeted region, wherein the plurality of tips of the medical device are not exposed with respect to the outer surface of the obturator,
   whereby the obturator is substantially blunt such that it exhibits a snag-resistant property, and wherein the obturator is dissolvable in the targeted region within a preconfigured time period.

2. The system of claim 1, further comprising:
   an interface element configured to engage an interface of the targeted region such that pressure is maintained within the targeted region.

3. The system of claim 2, wherein the interface element includes a convex portion that operates to seat the interface element at a selected location.

4. The system of claim 2, wherein the interface element is substantially transparent such that a user of the interface element can aim the obturator or the medical device.

5. The system of claim 4, wherein the interface element includes a magnification element that magnifies materials underlying the interface element.

6. The system of claim 1, further comprising:
   a tray operable to provide a mold for forming the obturator.

7. The system of claim 1, wherein the plurality of tips of the medical device are sharp and pierce the outer surface of the obturator such that the plurality of tips are not exposed.

8. The system of claim 1, wherein the medical device includes two or more legs each terminating at one of the plurality of tips, and wherein the legs are configured to hold a proximal end of a vessel for placement in the targeted region.

* * * * *